US008083066B2

(12) United States Patent
Bourely

(10) Patent No.: US 8,083,066 B2
(45) Date of Patent: Dec. 27, 2011

(54) METHOD AND MACHINE FOR AUTOMATICALLY INSPECTING AND SORTING OBJECTS ACCORDING TO THEIR THICKNESS

(75) Inventor: Antoine Bourely, La Tour d'Aigues (FR)

(73) Assignee: Pellenc Selective Technologies, Pertuis (FR)

( * ) Notice: Subject to any disclaimer, the term of this patent is extended or adjusted under 35 U.S.C. 154(b) by 619 days.

(21) Appl. No.: 12/159,629

(22) PCT Filed: Dec. 28, 2006

(86) PCT No.: PCT/FR2006/002900
§ 371 (c)(1),
(2), (4) Date: Jul. 25, 2008

(87) PCT Pub. No.: WO2007/077367
PCT Pub. Date: Jul. 12, 2007

(65) Prior Publication Data
US 2008/0302707 A1 Dec. 11, 2008

(30) Foreign Application Priority Data
Dec. 30, 2005 (FR) .................................. 05 13507

(51) Int. Cl.
*B03B 1/00* (2006.01)
*B03D 3/00* (2006.01)
(52) U.S. Cl. .............. 209/3; 209/11; 209/552; 209/555; 209/576; 209/939
(58) Field of Classification Search ................ 209/3, 11, 209/552, 555, 576, 939; 356/43
See application file for complete search history.

(56) References Cited

U.S. PATENT DOCUMENTS

| | | | | | |
|---|---|---|---|---|---|
| 4,118,309 | A | * | 10/1978 | Myers et al. ................. | 208/411 |
| 4,152,245 | A | * | 5/1979 | Abdul-Rahman et al. .... | 208/409 |
| 4,513,384 | A | * | 4/1985 | Rosencwaig ................ | 702/170 |
| 4,768,158 | A | * | 8/1988 | Osanai ........................ | 702/34 |
| 4,996,426 | A | * | 2/1991 | Cielo et al. .................. | 250/330 |

(Continued)

FOREIGN PATENT DOCUMENTS
FR 2 697 450 A 5/1994
(Continued)

*Primary Examiner* — Stefanos Karmis
*Assistant Examiner* — Michael E Butler
(74) *Attorney, Agent, or Firm* — Young & Thompson

(57) ABSTRACT

This invention has as its object an automatic process and machine for inspecting and sorting non-metallic objects. Process characterized in that it consists essentially in temporarily subjecting a surface or outside layer (4) of objects (1) passing in a single-layer stream to the caloric radiation of at least one remote heating means (5), so as to deliver to each of these passing objects (1) a non-altering heat pulse that is identical for all of the objects in terms of heat energy applied per unit of surface area in the conveying plane (2), then to acquire at least one thermal image of each of said objects by means of at least one linear or matrix thermal sensor (6), for example a thermal camera, this after a determined length of time has elapsed following the application of the heat pulse, then to classify or to categorize each passing object (1) based on data contained in its thermal image or images and to deliver a control or actuation signal for each object and, finally, to separate the passing objects (1) based on their class or category and/or the corresponding control or actuation signal that is delivered.

29 Claims, 3 Drawing Sheets

U.S. PATENT DOCUMENTS

| | | | |
|---|---|---|---|
| 5,344,026 A * | 9/1994 | Booth et al. | 209/580 |
| 5,628,409 A * | 5/1997 | Thomas | 209/577 |
| 6,112,903 A * | 9/2000 | Kimmel et al. | 209/11 |
| 6,367,968 B1 * | 4/2002 | Ringermacher et al. | 374/7 |
| 6,394,646 B1 * | 5/2002 | Ringermacher et al. | 374/7 |
| 6,592,252 B2 * | 7/2003 | Baba | 374/43 |
| 6,845,869 B1 * | 1/2005 | Graf von Deym et al. | 209/522 |
| 6,914,678 B1 * | 7/2005 | Ulrichsen et al. | 356/429 |
| 7,060,991 B2 * | 6/2006 | Reilly et al. | 250/443.1 |
| 7,222,738 B1 * | 5/2007 | Stockard | 209/552 |
| 7,419,298 B2 * | 9/2008 | Ouyang et al. | 374/5 |
| 7,549,789 B2 * | 6/2009 | Tralshawala et al. | 374/43 |
| 7,573,582 B2 * | 8/2009 | Mikami | 356/504 |
| 7,591,583 B2 * | 9/2009 | Foes et al. | 374/5 |
| 2002/0027943 A1 * | 3/2002 | Yokoyama et al. | 374/45 |
| 2004/0005147 A1 * | 1/2004 | Wang et al. | 392/418 |
| 2008/0144049 A1 * | 6/2008 | Ringermacher et al. | 356/630 |
| 2008/0257793 A1 * | 10/2008 | Valerio | 209/567 |

FOREIGN PATENT DOCUMENTS

| | | |
|---|---|---|
| GB | 2 278 440 A | 11/1994 |
| WO | 96/23604 A | 8/1996 |

* cited by examiner

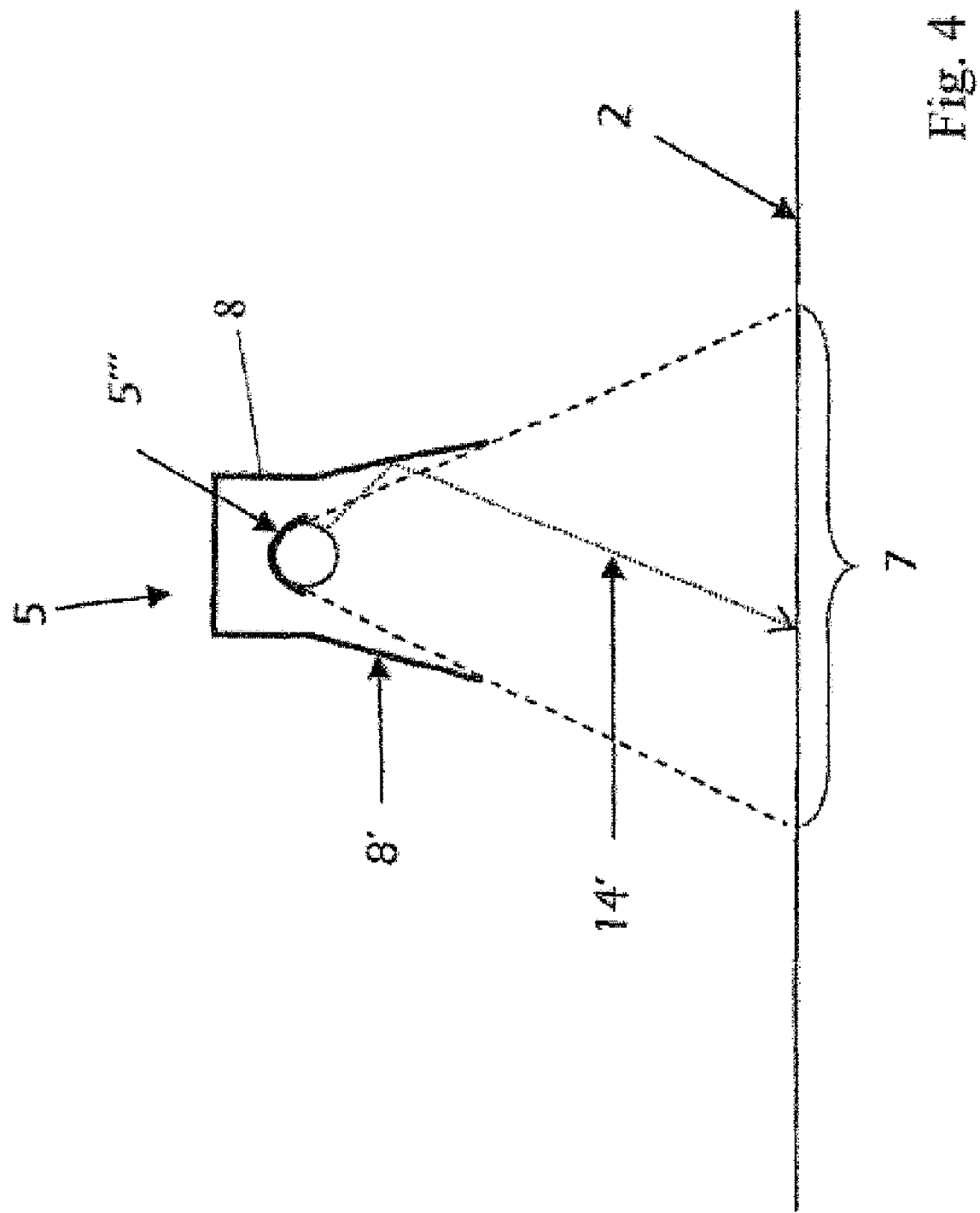

METHOD AND MACHINE FOR AUTOMATICALLY INSPECTING AND SORTING OBJECTS ACCORDING TO THEIR THICKNESS

This invention relates to the field of the characterization and successive physical separation of objects, articles, products or mixed analogs into multiple categories, more particularly the production of an automatic real-time sorting of a passing stream of such objects, articles and/or products.

This invention has as its objects an automatic process and machine for inspecting and sorting non-metallic objects that belong to at least two different categories, in particular with different thicknesses.

Numerous automatic processes and devices for inspecting and storing, using different types of electromagnetic radiation, and analyzing the radiation that is reflected or that passes through at the level of the stream of passing objects are already known. A machine of this type is disclosed in particular in the French Patent No. 2 822 235 and the Patent Application No. WO 02/074452 in the name of the Pellenc Company.

The known processes and devices for automatic characterization of the above-mentioned type do not make it possible to perform a differentiation of objects or articles that have different structures but that exhibit on the surface the same constituent material.

In addition, the zones for application of radiation and measurement being combined, this gives rise to problems of required space because of the fact that both the means for application of the incident radiation and for measurement of the reflected or transmitted radiation are combined in a reduced volume.

In addition, although these known solutions are relatively high-performing, they require particular types of radiations and therefore specific emitters and receivers and a high cost.

The general problem that is posed with this invention consequently consists in proposing a solution that makes it possible to overcome the above-mentioned drawbacks.

Furthermore, principles and certain applications of thermography, i.e., the technology that uses body-radiated heat, are known.

A body at ambient temperature radiates at a wavelength that is close to 10 μm, and this is all the greater as it heats. At 300-400° C., it emits toward 5 μm. An intensity that varies very quickly with the temperature is detected, and it is converted into a black and white image. An image in which the most brilliant objects are the hottest is thus obtained.

For several years, the thermographic technology has radically evolved, primarily in band 3 (7 to 12 μm): at this time, new generations of moderately-priced cameras are used, for example cameras of the thermometric type with microbolometers, which exhibit very advantageous characteristics:
  They operate without cooling devices;
  The temperature resolutions that are available are very fine, about 0.1° C., and even 0.01° C. Whereby no system is perfectly thermally balanced, primarily for slight temperature fluctuations, the contrast between the different objects of a scene is good;
  The spatial resolutions are good: 320×240 pixels is a common value;
  The response times are compatible with the video flows, or 25 images/second.

In the context of the active thermography, which is that of this invention and within the framework of which temperatures are measured after the products to be analyzed have been subjected to the same heat pulse, various implementations and applications are already known.

A standard application of thermography is the quality control of welding or bonding in metallurgy. The patent U.S. Pat. No. 4,996,426 has a method for detecting the presence of cracks or bad bonding within laminar, primarily metal, materials. It proposes the transfer of the heat image of the part (plane) by contact with a polymer foam roller. The hot tips (assembly by reflection) or the cold tips (assembly by transmission) point out the breaks in conductivity and therefore continuity defects in the material. The measurement is dynamic: the defect is visible only within a short window of time between the arrival of the heat flow on it and its complete bypass by this same flow. As soon as the provided heat is spread out evenly in the material, the defect is no longer visible. The method can be extended to the estimation of the depth of the defects, but the response dynamic then depends on the form and the nature of the defect.

To detect defects, the patent U.S. Pat. No. 6,914,678 also uses a laser that is controlled by a scanning system, moving at a constant speed over the entire surface of the object to be inspected and examining the temperature at a given and set distance from the heated zone, therefore after a set period. This document insists on the precise adjustment that is necessary for this period based on the material.

These technologies were passed on in the 1990's for the quality control of wood products, such as plywood plates. In this application, the transfer times are considerably longer than for the metals, and the heating of the products is on the order of 5° C. The principle, however, is identical, and the defect ceases to be visible after the temperature has spread out evenly in the material. The method has been extended to food products (chocolates with hazelnuts, candy) with detection of foreign bodies inserted in the mass of the product.

The thermography can also be applied to the detection of foreign bodies that are difficult to distinguish otherwise. Thus, the filing DE 43 17 513 proposes the detection of clumps of earth and rocks in a stream of potatoes. It is the polarization of the reflected thermal radiation that develops differently based on the density of the products that are being considered, and it is measured by reflection, therefore simultaneously with the heating.

The thermography can also be used to measure the thicknesses of walls, as described in the document "Métrologie thermique: des matériaux jusqu'aux structures [Thermal Metrology: Materials up to Structures]," author: J. C. Krapez, Jun. 23, 1999. In this document, it is proposed to measure the heating after a surface heat pulse and a temperature stabilization. The method is described as slow, because it addresses parts of several millimeters of thickness. Other methods are proposed to accelerate the reading by analysis of the temporal heating profile, but they call for acquiring and processing numerous thermal images.

Furthermore, other applications of thermography are described in the following documents:
  GB-A-2 278 440 describes a system that makes it possible to sort products of different natures (diamonds/stones or gravel) based on their respective emissivity. Its implementation requires a uniform temperature of products before treatment.
  WO 96/23604 describes a system for separating products producing a preliminary heating of said products and then a segregation of the latter based on the status of their temperature relative to predetermined temperature ranges. However, this document does not absolutely specify on what bases rests the discrimination that is performed.

FR-A-2 697 450 discloses a process and a device for sorting vegetable products. The discriminating factor is the moisture level that makes it possible to differentiate the good products (fruits and vegetables) from the products to be eliminated (cores, stems, lignified parts) based on their nature (high level/low level).

US-A-2002/0027943 proposes a system and a process for sorting packages based on their nature (constituent material). A prolonged heating whose energy cost during use is unacceptable and that does not allow high rates is noted.

It emerges from the analysis of the prior art above that none of the above-mentioned documents specifically mentions the processing of products of very small thickness, in particular on the order of one millimeter or less than one millimeter. The media that are analyzed within the scope of these prior publications appear as either semi-infinite on the measurement time scale (the thermal flux has not reached the opposite wall of the object before the measurement) or thick enough so that the heat energy is not also uniformly distributed in the product. Most of the methods that are implemented are therefore relatively complex and long and rely on the recording of temporal temperature profiles.

This invention aims at proposing a reliable solution that is simple and energy-frugal for using the properties of thermography applied to relatively thin products or to a thin surface layer in the context of the characterization and the real-time separation of objects, articles or products of the same nature that come in the form of a passing stream.

For this purpose, this invention has as its object an automatic process for inspecting and sorting non-metallic objects that belong to at least two different categories and pass in an essentially single-layer stream on a conveying plane of a conveyor belt, whereby said process consists essentially in temporarily subjecting a surface or outside layer of said objects to the caloric radiation of at least one remote heating means, so as to deliver to each of these passing objects a non-altering heat pulse that is identical for all of the objects in terms of heat energy applied per unit of surface area in the conveying plane, then to acquire at least one thermal image of each of said objects by means of at least one linear or matrix thermal sensor, for example a thermal camera, this after a determined length of time has elapsed following the application of the heat pulse, then to classify or to categorize each passing object based on data contained in its thermal image or images and to deliver a control or actuation signal for each object and, finally, to separate the passing objects based on their class or category and/or the corresponding control or actuation signal that is delivered, process characterized:

in that the data of the image or the thermal image(s) from each passing object are processed to perform discrimination or characterization of the objects in terms of the thickness of the surface layer affected by the radiation, whereby the constituent material of said surface layer at least of the passing objects is identical for all of the objects, in that for a given object, the length of time that elapses between the application of the heating radiation and the thermal imaging is, on the one hand, sufficient for ending in an essentially homogeneous distribution of the caloric energy that is absorbed in said surface layer such that the temperature difference after heating said objects on the surface is essentially inversely proportional to the thickness of this surface layer, while being, on the other hand, short enough so that the phenomena of lateral thermal diffusion, cooling by radiation and convection are negligible.

The invention also relates to an automatic machine for inspecting and sorting non-metallic objects, such as those emerging from claim 12.

The invention will be better understood using the description below, which relates to preferred embodiments, provided by way of non-limiting examples and explained with reference to the attached schematic drawings, in which:

FIG. 4 is a view that is similar to FIG. 2 of another variant embodiment of lighting means that form part of the machine according to the invention.

Figure 1:
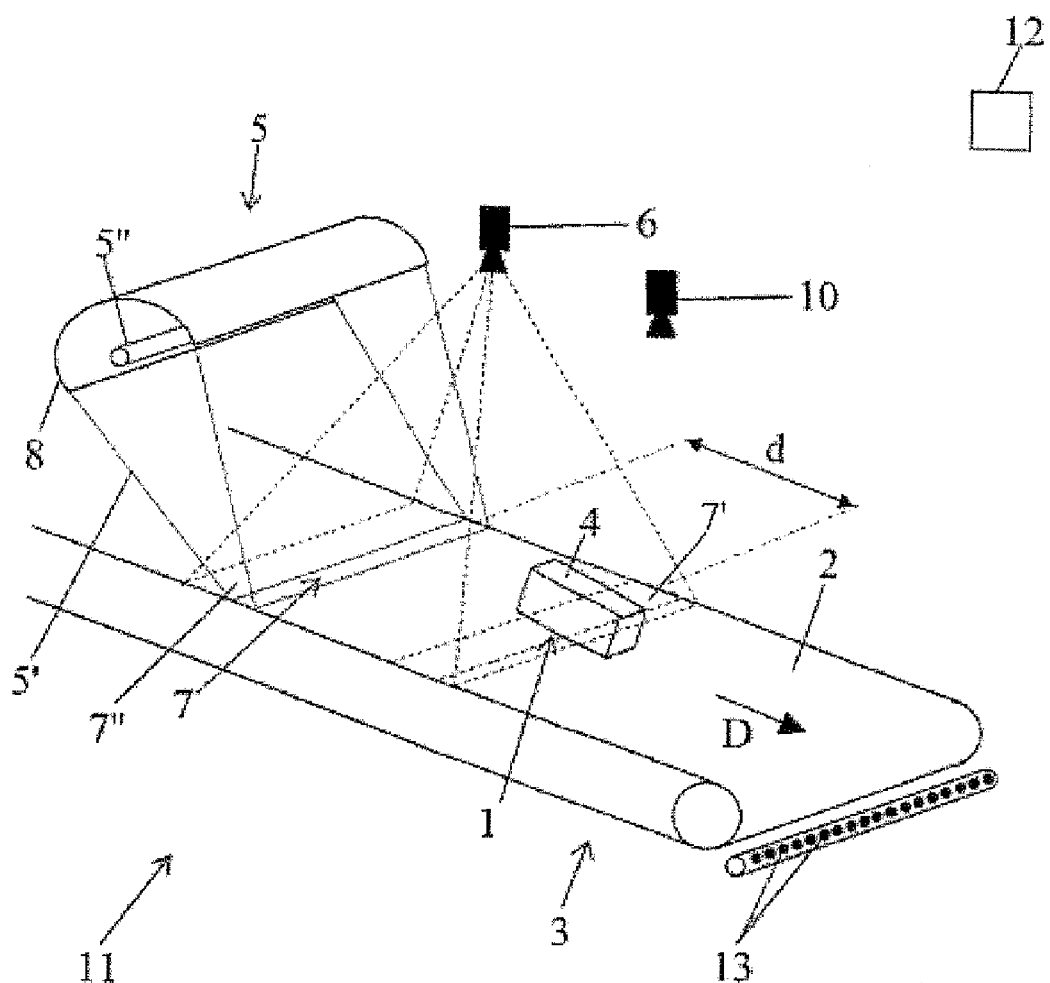
FIG. 1 is a partial perspective schematic representation of a machine according to a first variant embodiment of the invention for the implementation of the process according to the invention.
Figure 3:
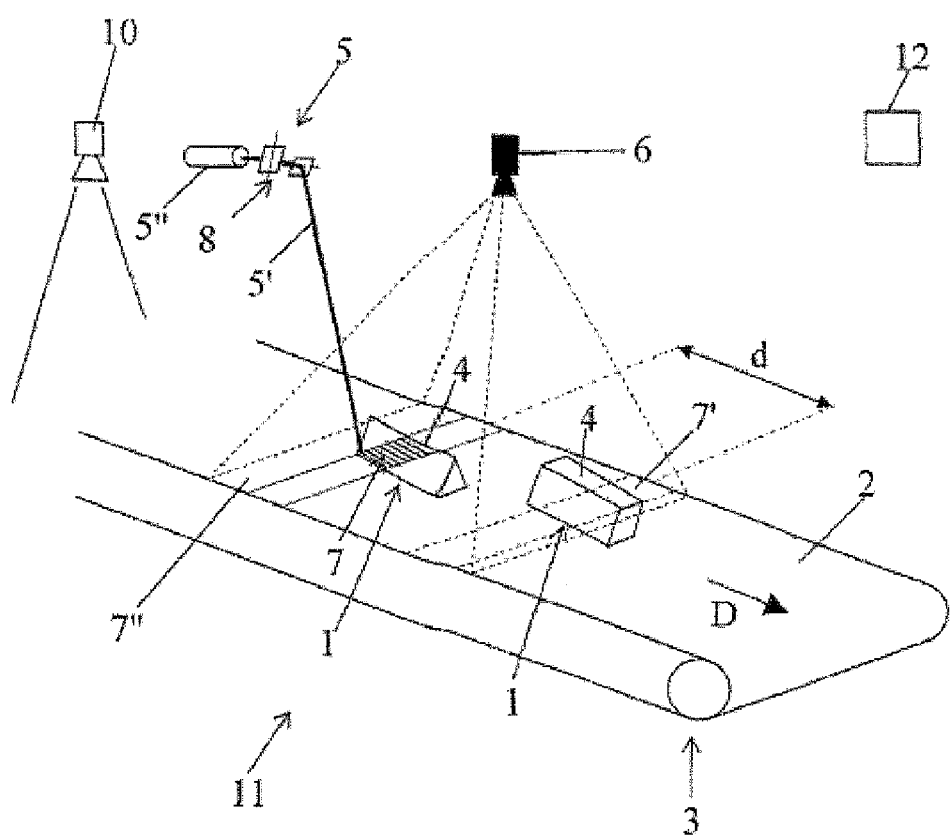
FIG. 3 is a perspective schematic representation of a second variant embodiment of the machine according to the invention.

As FIGS. 1 and 3 in particular of the accompanying drawings illustrate, the invention relates to an automatic process for inspecting and sorting non-metallic objects 1 that belong to at least two different categories and that pass in an essentially single-layer stream on a conveying plane 2 of a conveyor belt 3 for the purpose of performing at least one type of discrimination or characterization at the level of these objects based on at least one constituent or constructive characteristic of the latter.

More particularly, this process essentially consists of temporarily subjecting a surface or outside layer 4 of said objects 1 to the caloric radiation of at least one remote heating means 5 so as to deliver to each of these passing objects 1 a non-altering heat pulse that is identical for all of the objects in terms of thermal energy that is applied per unit of surface area in the conveying plane 2, then to acquire at least one thermal image of each of said objects by means of at least one linear or matrix thermal sensor 6, for example a thermal camera, this after a determined length of time has elapsed following the application of the heat pulse, then to classify or to categorize each passing object 1 based on the data that are contained in its thermal image(s) and to deliver a control or actuation signal for each object, and, finally, to separate the passing objects 1 based on their class or category and/or the corresponding control or actuation signal that is delivered.

According to the invention, this process is characterized in that the data of the thermal image or images from each passing object 1 are processed to perform discrimination or characterization of the objects in terms of thickness of the surface layer 4 that is affected by the radiation, whereby the constituent material of said surface layer 4 at least of the passing objects 1 is identical for all of the objects.

This process is also characterized in that for a given object 1, the length of time that elapses between the application of the heating radiation and thermal imaging is adequate for ending in an essentially homogeneous distribution of the caloric energy that is absorbed in said surface layer 4, such that the temperature difference after surface heating of said objects is essentially inversely proportional to the thickness of this surface layer 4, while being short enough so that the phenomena of lateral thermal diffusion, cooling by radiation and convection are negligible.

In this document, "negligible" characterizes phenomena whose influences have very little or no effect on the data provided by the thermal images and the results of the exploitation of these images (typically less than 10%, and even less than 5% of variation in the data provided).

Consistent with a very advantageous variant embodiment, the discrimination or the characterization of said passing objects 1 is performed on the basis of differential data or by differential exploitation of data, obtained either from thermal images that are taken before and after application of the caloric radiation that is emitted by the heating means 5 or from the single thermal image taken after application.

Preferably, the heat pulse can affect the exposed surface layer 4 of each passing object 1 over its entire surface or only in certain zones.

The intensity data provided by the thermal images directly make it possible to perform discrimination and therefore a sorting between the different categories of passing objects.

In connection with a typical characteristic of the process according to the invention, the surface layer 4 that is involved for performing the discrimination or the categorization of objects 1 has a thickness of greater than 20 μm, advantageously between 20 μm and 2 mm, preferably between 30 μm and 1 mm, and the length of time that elapses between the application of the caloric radiation and the thermal imaging is on the order of several tenths of a second, preferably between 50 ms and 600 ms, and more preferably between 250 and 400 ms.

When it can be guaranteed that all of the objects 1 that are intended to be processed by the process have an identical and homogeneous temperature at least at the level of their outside layer(s), it is possible to remove the thermal imaging before application of the heat pulse, and the discrimination or the characterization of the passing objects is then performed on the basis of the single thermal images taken after controlled heating of said objects by the corresponding means 5, whereby the starting or initial thermal state is identical for all of the objects 1.

However, so as to be able to perform a reliable thermographic discrimination regardless of the thermal state of the various objects 1 to be analyzed before the application of the radiation of the heating means, i.e., even when the various objects have initial thermal states that are different, the process may consist in taking a partial or total thermal image of each passing object 1 before its exposure to the radiation of the heating means 5, whereby the discrimination or the characterization of said passing objects 1 is performed on the basis of differential data obtained from said thermal images taken before and after application of the caloric radiation emitted by the heating means 5, whereby the images before and after exposure are taken by the same thermal sensor 6 or by two different sensors.

Figure 2:
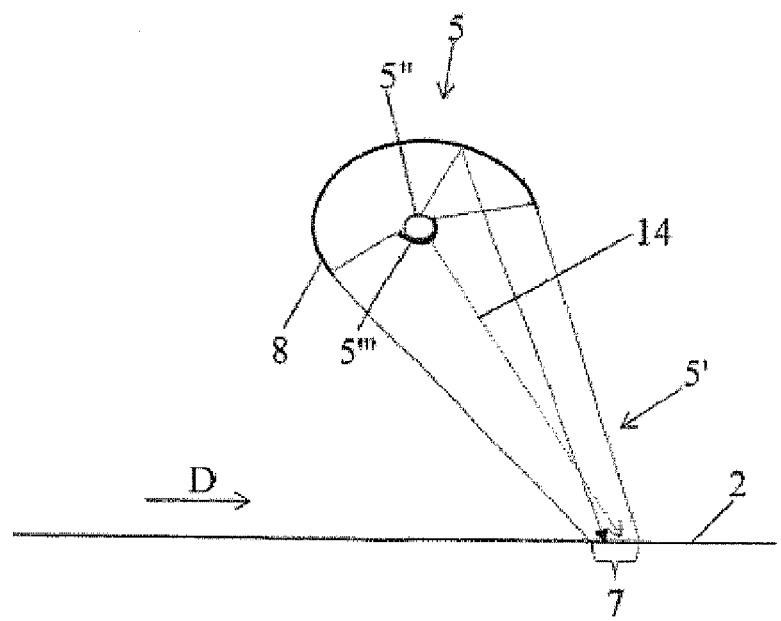
FIG. 2 is a detail cutaway view that shows the heating means and a portion of the conveying plane of the machine that is shown in FIG. 1.

Consistent with a first practical embodiment of the invention, emerging from FIGS. 1 and 2 of the accompanying drawings, the deposit of caloric energy that results from the application of the radiation 5' emitted by the heating means 5 is essentially uniform and spread out evenly over the entire exposed surface 7 at the level of the conveying plane 2. Such an arrangement requires the implementation of a suitable heating means 5 as well as a determined positioning of this means relative to the conveying plane 2.

Consistent with a second practical embodiment of the invention, emerging from FIG. 3 of the accompanying drawings, the deposit of caloric energy carried out by the radiation 5' that is emitted by the heating means 5 is by nature intermittent and limited to localized zones of the exposed surface 7 at the level of the conveying plane 2, such as, for example, segments of lines or bands that extend in the direction in which the objects pass or the conveyor belt 3 moves, optionally circumscribed in the regions corresponding to objects 1 as they pass.

Performing such an intermittent application of the caloric energy in the exposed zone or the heating zone 7 of the conveying plane can be achieved by using either a radiation source with discontinuous or intermittent emission or a source with continuous or constant emission whose radiation is interrupted spatially by an intermediate element (mask) between the source and the conveying plane. The first solution makes it possible, of course, to produce a gain in consumed power.

In connection with the second above-mentioned embodiment, it may advantageously be provided that the discrimination or the characterization of each passing object 1 is carried out on the basis of the single thermal image taken after exposure, by differential exploitation of the data from the irradiated zones and non-irradiated zones of the surface, and therefore of the exposed surface layer 4 of the object in question.

As emerges from FIGS. 1 to 3 of the accompanying drawings, the window of application in the conveying plane of the caloric radiation defines an exposed surface 7 and therefore a heating zone in band form, preferably of small width, or of a line that extends essentially crosswise relative to the direction D in which the conveyor belt 3 moves or the objects 1 pass.

In addition, in a preferred manner, the caloric radiation is a focused radiation, preferably of the infra-red type or with a majority infra-red component, and it is delivered by means of an application means 8 that is located at least a minimum distance above the conveying plane 2, in particular at least slightly higher than the maximum height of the passing objects 1.

Still in connection with the second above-mentioned embodiment, it may be provided that the portion of the caloric radiation that is produced by the heating means 5 and directed toward the conveying plane 2 is blocked by a reflective mask 5''' such that all of the radiation emitted by said heating means 5 is applied to the exposed surface 7 of the conveying plane 2 by a reflective and concentrating element that forms part of said heating means 5 and forms an application means 8.

In particular, when the stream of objects 1 exhibits a great variety (in terms of constituent materials, structures, compositions, etc.) and/or when the discrimination or characterization is to be extremely reliable and can be based on several criteria and parameters of analysis, the process may also consist in acquiring additional data relating to the passing objects 1 by means of at least one additional sensor 10, for example selected from the group that is formed by magnetic detectors, spectrometers, and black and white or color vision cameras, and in combining the results of the exploitation of these additional data with the results of the exploitation of the data contained in the thermal image or images to perform the discrimination or the characterization of said passing objects 1.

When said at least one additional sensor 10 is placed upstream from the heating means 5 in the direction of the passing of objects 1 (or with an inspection window upstream from the heating zone 7), the data acquired by this sensor 10 can be used as a variant or in a supplementary manner to control said heating means 5 when the latter has an intermittent application.

This invention also relates to, as the accompanying figures show diagrammatically and partially, an automatic machine 11 for inspecting and sorting non-metallic objects 1 that belong to at least two different categories and that pass in an essentially single-layer stream on a conveying plane 2 of a conveyor belt 3 (also forming part, if necessary, of the machine 11), making it possible to perform at least one type of discrimination or characterization at the level of these objects 1 based on at least one constituent or constructive characteristic of the latter.

This machine 11 comprises, on the one hand, at least one remote heating means 5 that can temporarily subject a surface or outside layer 4 of said passing objects 1 to its caloric radiation so as to deliver to each of these passing objects a non-alternating heat pulse that is identical for all of these objects in terms of thermal energy that is applied per unit of surface area in the conveying plane 2, and, on the other hand, at least one linear or matrix thermal sensor 6, for example a thermal camera, placed at a determined distance downstream from said at least one heating means 5 in the direction of passing and able to acquire at least one thermal image of each of said objects and, finally, at least one processing unit 12 that is able to classify or categorize each passing object 1 based on the data contained in its thermal image or images and to deliver a control or actuation signal for each object, whereby said at least one processing unit 12 is connected to at least one means 13 that can separate said passing objects 1 based on their category or class and the corresponding control or actuation signal that is delivered.

This machine is characterized in that the distance d that separates the zone in which the thermal radiation or each thermal radiation is applied, or the heating zone 7, from the zone in which the respectively associated thermal imaging zone or each respectively associated thermal imaging zone 7' is applied, is, on the one hand, long enough so that the caloric energy that is absorbed in a surface layer 4 of the constituent material of each passing object 1 has an essentially homogenous distribution in this layer, and, on the other hand, short enough so that the effects of the phenomena of lateral thermal diffusion, cooling by radiation and convection are negligible.

It is also characterized in that the data of the thermal image or images from each passing object 1 are processed to perform discrimination or characterization of the objects in terms of the thickness of said surface layer 4, whereby the constituent material of the surface layer 4 at least of the passing objects 1 is identical for all of the objects.

Preferably, the processing unit 12 performs the discrimination or the characterization of said passing objects 1 on the basis of differential data or by differential exploitation of data, obtained either from thermal images taken before and after application of the caloric radiation that is emitted by the heating means 5, or from the single thermal image taken after application.

According to a characteristic of the invention, the conveyor belt 3 that forms the conveying plane 2 has a constant displacement speed, and said at least one heating means 5 and said at least one thermal sensor 6 are placed above said conveying plane 2. In addition, the distance d that separates the zone in which the thermal radiation or each thermal radiation is applied, or heating zone 7, from the zone in which the respectively associated thermal imaging zone or each thermal imaging zone 7' is applied is, on the one hand, short enough so that the effects of the phenomena of lateral thermal diffusion, of cooling by radiation, and of convection are negligible, and, on the other hand, long enough so that the caloric energy that is absorbed in a surface layer 4 of the constituent material of each passing object 1 has an essentially homogeneous distribution in this layer.

As the figures of the accompanying drawings also show, the radiation 5' that is delivered by the remote heating means 5 is directed so as to affect a narrow band or a line of the conveying plane 2 that forms an exposed surface or a heating zone 7 and that extends essentially crosswise relative to the direction D in which the conveyor belt 3 moves or the objects 1 pass, and said radiation 5' is a focused radiation, preferably of the infra-red type or at least with a majority infra-red component.

Consistent with a first embodiment of the machine 11 according to the invention, emerging from FIGS. 1 and 2, the heating means 5 consists of the combination, on the one hand, of a radiation source 5" with a tubular focal point or an alignment of radiation sources with essentially specific or elongated focal points with, on the other hand, a deflector element 8 and a radiation-concentrating element 5', and the two above-mentioned components 5" and 8 that form said heating means 5 have a shaped extension, extend crosswise to a substantial portion of the width of the conveying plane 2, preferably essentially over this entire width, and carry out in mutual cooperation a deposit of essentially uniform and homogeneous caloric energy over the entire surface of the heating zone 7 in belt form of the conveying plane 2 that receives the focused radiation.

Advantageously, the tubular radiation source 5" consists of a radiant tube that comprises a reflective mask or a layer 5''', for example in the form of a metallic deposit, on the surface of said tube 5" that is rotated toward the conveying plane 2, such that approximately the entire radiation that is emitted is directed toward said conveying plane 2 by the deflecting and concentrating element 8 that is combined with said radiant tube 5", for example of the type that emits a radiation in the middle infra-red range, preferably with wavelengths that are longer than 2000 nm.

Preferably, the thermal sensor or sensors 6 carry out, for each passing object 1, an imaging before and after the exposure of said object to or with a caloric radiation 5', and the processing unit 12 performs discrimination or categorization of said passing objects 1 on the basis of differential data obtained from their thermal images that are acquired before and after exposure to said caloric radiation 5'.

Consistent with a second embodiment of the machine 11 according to the invention, shown in FIG. 3 of the accompanying drawings, the heating means 5 consists of a laser source 5", of the continuous or intermittent emission type, combined with an application device 8 with two-dimensional scanning (for example, in the form of two pivoting mirrors with perpendicular axes), whereby the deposit of caloric energy is of an intermittent nature and limited to the localized zones of the exposed surface 7 at the level of the conveying plane 2, such as, for example, segments of lines or bands that extend in the direction in which the objects pass or the conveyor belt 3 moves, optionally circumscribed in the regions corresponding to objects 1 as they pass.

Within the scope of this second embodiment, the processing unit 12 can perform discrimination or characterization of each passing object 1 on the basis of the single thermal image taken after exposure, by differential exploitation of the data from irradiated zones and non-irradiated zones of the surface 7, and therefore the exposed part of the surface layer 4 of the object 1 in question.

For the purpose of optimizing the application of the caloric radiation 5', in connection with said second embodiment, and therefore the energy consumption of the intermittently depositing heating means 5, the machine 11 can also comprise a device for locating and delimiting the apparent surface of passing objects 1 on the conveying plane 2 that is located upstream from the heating means 5 in the direction of passage, whereby the data acquired by this device for locating and delimiting the apparent surface are used to control said heating means 5 in the form of a [laser source 5"/application device 8 with scanning] unit.

For the purpose of increasing the performance levels of the machine 11 in terms of discrimination, the latter optionally can acquire—in real time—additional data relative to the passing objects with a nature other than thermal.

For this purpose, it can then comprise at least one additional sensor 10 that is selected from the group that is formed by the magnetic detectors, spectrometers, black and white or color vision cameras, and the results of the exploitation of these additional data are combined in a processing unit 12 with the results of the exploitation of the data that are contained in the thermal image or images for performing the discrimination or the characterization of said passing objects 1.

The above-mentioned device for locating and delimiting/distinguishing objects 1 optionally can consist of such an additional sensor 10 placed upstream from the heating zone 7.

It is well understood that the machine 11 further comprises, in addition to the means described explicitly above and illustrated in the figures, all of the other means (equipment and software) that are necessary for the implementation of the process described above, including its programming by a user or operator and its linking with other installations or systems. These other means being known or within the scope of one skilled in the art, they will not be described any further in this document.

So as to better illustrate the different practical embodiments that are possible for the invention, designed to solve different types of sorting, several concrete embodiments and applications of the process and the machine according to the invention are described in more detail below.

The various embodiments and applications mentioned below have in common rapidly passing objects 1 (1 to 3 m/s), spread in a single layer and stabilized on a plane conveyor belt 3, in accordance with two filings of the above-mentioned patents of the Pellenc Company.

The general principle is presented in FIGS. 1 and 3.

The machine 11 comprises at least one heating means 5 of the passing objects or products 1, which integrates as a radiation source 5" either a laser source or a thermal-type lamp (Globar, incandescent lamp, halogen lamp, Xenon flash lamp, etc.) that produces the energy that is preferably located in wavelengths that are greater than 2000 nm, whereby the unit is set above a conveyor belt 3, and an application means 8 of the deviation or focusing type, for example an elliptical mirror or reflector, which creates a zone 7 of strong lighting and of small width over the entire width of the conveyor belt 3. Any object 1 as it passes on this conveyor belt is therefore subjected to a heat pulse of several milliseconds, according to the characteristics of the heating means 5.

A linear or matrix thermal camera 6 visualizes at least one measurement zone 7' where image acquisition is done after diffusion of the heat in the surface layer 4 of the object 1 or product. A control or reference zone 7" that is placed before heating can also be visualized to indicate the surface temperature of objects 1 before heating. If the camera 6 is a matrix camera, the field of vision can be selected as indicated in FIGS. 1 and 3, such that the same camera visualizes the two zones 7' and 7" at the same time. If the camera 6 is a linear camera, the zone 7" should be visualized by a second camera, not shown, and preferably identical.

The heating zone 7 and the rear imaging zone 7' are separated by the distance d, variable according to the application.

Optionally, another sensor 10 of a different nature (color vision, infra-red spectrometer, etc.) can be placed on the same conveyor belt, before or after the camera 6. The information that is provided by the sensor 10 can be combined with that provided by the camera 6 to result in a combined classification of objects 1, by a suitable computer and algorithm (processing unit 12). At the end of the conveyor belt, some of the nozzles of the nozzle bar that form the separation means 13 are actuated to eject the selected objects.

The objects to be sorted 1 are, for example, cardboard-paper, plastics (packages, films, bags, ground waste of electronic or automobile origin) or biological wastes to be sorted for composting or other biological treatment.

The objects 1 are generally stored in a sorting center primarily in two forms, loose or in balls. In general, they remain there long enough for their surface temperature to be spread out evenly, but this is not always the case, in particular in the case of outside storage (effects of the sun, rain, frost). After loading on the sorting line integrating the machine 11, their temperature can therefore vary in a range from one to several degrees. Alternately, in a recycling center, the objects 1 can be passed through a hot washing phase just before the sorting zone, and their temperature is then spread out more evenly.

Each object 1 is first accelerated on the conveyor belt 3 and then stabilized. The speed of the conveyor belt is optimized based on the nature of the objects 1 to ensure a spreading on a single layer, while avoiding the sliding or rolling for the large majority of the objects. The speeds that are generally adopted vary from 1 to 3 m/s.

Each object 1 first passes through the control zone 7", where a first thermal image can be acquired: it indicates the starting temperature of the object 1. In general, the object clearly becomes detached by its colder temperature on the bottom of the conveyor belt 3, because the latter is continuously heated by the means 5, whereas the object makes only a rapid passage.

The object 1 then passes through the zone 7 where it receives a heat pulse that is also distributed over its entire surface layer 4. This zone 7 has a preferred width of 5 to 10 cm. This width is to be reduced to characterize as well as possible the moment of passing.

While the object 1 travels through the distance d, the heat that is received is spread out evenly in its surface layer 4 if the object is thin (less than 0.5 mm), and it is diffused in the depth of the object if the latter is deep or thick (see modeling below). The distance d is selected based on the nature of the materials and the surface layer thicknesses of the objects to be sorted. Its order of magnitude is 100 to 600 mm. During this travel, the cooling by radiation of the surface layer of the object has a negligible range, as will be shown below.

When the object passes into the zone 7', a second thermal image is acquired and makes it possible to know the temperature of the object 1 after thermal stabilization. The difference in temperatures before and after heating provides the overall heating of the object 1 that is considered.

One (or more) other sensor(s) 10, placed in the same zone, can provide important additional information and in particular:

The position of the object 1 on the conveyor belt 3, in the case where the thermal contrast is inadequate to locate it well in the thermal images: the most suitable sensor 10 is a color vision camera;

Other criteria of appearance, in particular its color and the characteristics of its printed patterns (vision camera);

The constituent material of the object, provided by, for example, an infra-red spectrometer as described in the above-mentioned French filing and the PCT filing of the Pellenc Company.

If the constituent material of the object 1 is known, the measured heating makes it possible to deduce the thickness of the first layer or surface layer 4. It thus is possible, for example, to differentiate paper from cardboard, because they differ only by their specific mass (more or less than 224 g/m² for the French standards), which mass is directly linked to the thickness thereof.

Finally, the machine 11 in the form of a combined classifier that uses the data from sensors 6 and 10 makes it possible to make a decision as to whether or not to eject each object 1. Only a single row of ejection nozzles 13 has been shown here, but this example is in no way limiting: it is possible in particular to have a ternary sorting, with two parallel rows of nozzles, on the same side or two opposite sides of the stream of products or objects 1.

A variant of the operation above is to take more than two images during the passing of the object, which is easy with a matrix camera. It may actually be advantageous in some cases to use intermediate images, taken either during the heating phase or during the heat diffusion phase.

So as to allow a better understanding of the invention and to demonstrate its theoretical foundations, it may be advantageous to have recourse to a thermal modeling of the exploited phenomena.

Time it Takes for Heat to Spread Out Evenly in a Thin Object: The evolution of an object after a heat pulse is governed by the equation of the heat, which is written for a single dimension and in the absence of thermal sources:

$$\partial T/\partial t = \alpha \cdot \partial^2 T/\partial x^2$$

Here, T is the temperature, t is the elapsed time, x is the depth, and α is the diffusivity of the product.

In a semi-infinite medium, i.e., with a large thickness relative to the time of thermal diffusion, this time is provided in the literature by:

$$Td = e^2/4\alpha, \text{ where e is the thickness that is attained by the thermal flux.}$$

If, at the end of this period, the limit of the thin layer that constitutes the object is reached, the diffusion stops, and the temperature is spread out evenly during the following phase. It is estimated that this homogenization period, counted from the heat pulse, is Th=2. Td.

In the case of the cardboard paper, α is equal to 0.14 mm²/s. Td=18 ms for e=100 μm, and therefore Th=36 ms.

Furthermore, we note that if the heat pulse is located in a single zone of the surface, it diffuses only very slowly on the sides. For 1 mm of lateral diffusion, there is $$Td = 1.8 \text{ s, and for 2 mm, there is } Td = 7.2 \text{ s.}$$

It is therefore possible to state that the heat diffuses quickly (in one fraction of a second) into the thickness of the object, but that its lateral diffusion is negligible on our time scale. The same conclusions are valid for the plastics, whose diffusivities are close, and the thicknesses a bit larger (up to 500 μm, corresponding to Td=400 ms).

Final Heating Calculation for a Thin Cardboard: As a calorific capacity of the paper or cardboard, that of pine is taken: C=920 kJ/m³·K. If the total absorbed energy (case of a machine that is 800 mm in width) is 2000 W, and if the conveyor belt passes at 3 m/s, this energy is distributed as follows: 2000 J/s/(3 m/s×0.8 m)=833 J/m². For a cardboard that is 200 μm of thickness, this energy flow is distributed over $2 \cdot 10^{-4}$ m, or a volume density W=4165 kJ/m³. The heating is then W/C=4.5° C. For thin paper of 50 μm, the same reasoning provides 18° C.

This is therefore very significant heating that is easy to measure even with entry-level product line cameras. For products that are stored at a homogeneous temperature, this heating can even be adequate to make the control image unnecessary before heating.

Cooling by Radiation of the Heated Objects:

The Stefan-Boltzmann formula: $W = \sigma \cdot T^4$ can be applied to objects at ambient temperature, which provides the order of magnitude of the stream that is reemitted by radiation by the heated objects. At 300 K (27° C.), W=460 W/m², or 0.046 W/cm².

In addition, the radiation that is received by the object of its environment, whose temperature is very close, broadly compensates for this emission. The net flow is calculated by differentiating the formula around the ambient temperature of 300 K, for a temperature difference ΔT with the surrounding medium:

$$\Delta W = 4 \cdot \sigma \cdot T^3 \Delta T = 6.16 \cdot \Delta T$$

If, for example, the maximum value found above, or the most unfavorable, is taken, $$\Delta T = 18° \text{ C., then } \Delta W = 111 \text{ W/m}^2.$$

In this reasoning, the heat transfer by conduction into the following paper cardboard layers is disregarded: actually, the existence of even a small air space between the two layers enables the primary heat transfer to be done by radiation downward and not by conduction. Nevertheless, it is necessary to consider cooling on the two faces of this surface layer, or here ΔW'=222 W/m², where the m² are those of the heated surface (a single face).

If the heating phase provided approximately 800 J/m² (see above), the heat is evacuated only slowly by radiation (in more than 4 seconds for the thinnest paper, and up to one minute for a thick cardboard). It is therefore possible to disregard the cooling by radiation of these objects between the two instances of imaging mentioned, spaced by at least one half-second.

As already indicated above, the heating means 5 can come in various embodiments, each accounting for specific advantages and limitations.

A first possibility of carrying out the controlled heating of objects 1 consists in implementing middle infra-red radiation (MIR).

To ensure both a low penetration depth and a strong absorption, independent of the dying and inks, a concentrated lighting on the wavelengths of greater than 2000 nm is desirable. The absorbance in this range is greater than 80% for all of the organic products.

From the very fact of the strong absorption, the penetration depth of the radiations is low (beyond 3000 nm, attenuation of 90% after about 20 μm for water), which guarantees surface heating. It is thus ensured that only the first layer of the product is affected by the flash of heat. We note that this reasoning also means that too thin a product does not stop all of the radiation: a plastic bag that is 10 μm thick will collect only 10 to 50% of the energy depending on the wavelengths.

The diagram of a variant embodiment of the heating means 5 in the form of a lighting system according to the invention is presented in FIG. 2 of the accompanying drawings.

It is possible to produce such lighting with a cylindrical radiant tube 5". These tubes are standard industrial components of the ink-drying systems or glass-melting furnaces. Their costs are moderate, and their service lives are counted in years. With a surface temperature of 830° C., or 1100° K., radiated energy W=8.3 W/cm² is calculated according to the Blackbody Law.

The wavelength of the emission peak is λp=2630 nm.

It is seen that this temperature is suitable for our problem. For this temperature, the radiation of a tube that is 1 cm in diameter is enough to provide 2500 W per linear meter.

It is important to concentrate the heat pulse in a narrow band 7 in the axis in which the products pass. For reasons of product circulation (heights of passage greater than 350 mm) as well as for safety reasons (risk of fire), the lighting in general cannot be close to the conveyor belt. According to the invention, it is possible, nevertheless, to concentrate the heat flow: an elliptical reflector 8 is placed around the tube 5", and it is designed so that one of the focal points is the tube itself, whereby the other is close to the conveyor belt. Thus, any ray that passes through the reflector 8 is reflected so as to touch the conveyor belt in the zone 7. If, for example, the distance from the tube to the bottom of the reflector is approximately 12 cm, and the distance from the tube to the conveyor belt is approximately 50 cm, the zone 7 has a width of approximately 5 cm over the conveying plane 2 that is formed by the conveyor belt 3.

In addition, for the selected temperatures, it is possible to metallize half the tube 5" by placing a layer 5''' on its surface that is intended to be rotated toward the conveying plane 2. This blocks the essential part of the emission in the metallized zone: the rays 14 are not emitted or are very weakly emitted. The heat then radiates only into the half-space that is located beside the reflector 8. By metallizing the lower side, any direct lighting that would impair the instantaneous nature of the heating is eliminated, and all of the rays are forced to pass through the reflector, which optimizes the yield: zone 7 receives almost all of the radiated heat.

However, the embodiment that is indicated in FIG. 2 is purely by way of indication.

In all of the cases where a great distance from the tube 5" to the conveyor belt 3 is not necessary, it is possible to place the tube close to the conveyor belt, for example at about 20 cm. In this case, it is possible to eliminate the reflector 8 and to use only the metallized layer 5''' to limit the angular area of the radiation, optionally completed by a reflective and concentrating means. In this case, it will be advantageous for the zone 5''' to be placed toward the top, and the direct radiation is done toward the bottom.

FIG. 4 of the accompanying drawings illustrates a variant embodiment of the heating means 5 relative to the one that is shown in FIG. 2.

The radiating source that is shaped, for example, in the form of a tube is provided with a reflective layer 5''' that limits the angular diffusion of the radiation and is located on the face of the tube that is opposite to the conveying plane 2.

The action of this limiting layer of the diffusion angle advantageously can be completed by a reflector 8 that consists of, for example, upper and lateral reflective parts, for example portions of plane mirrors. These means make it possible to direct the rays that are emitted by the tube toward the conveying plane by concentrating them, but without focusing them.

The reference 14' designates a ray that is retracted into the zone 7 of the conveying plane using the reflector 8.

Another possibility for carrying out the controlled heating of the objects consists in implementing a halogen lighting.

Actually, it is also possible to produce a heat pulse by a halogen tube that is combined with an elliptical reflector, as described in the patent application mentioned above. This makes it possible to use the same lighting for the infra-red spectrometer and for the thermal camera, and this makes possible very good focusing of the lighting on a band 7 of less than 3 cm of width.

In contrast, this method has several limitations:

It is not possible to metallize the half-tube 5", and half of the energy is not focused. The direct rays that reach the conveyor belt 3 without passing through the reflector 8 also heat the products, but the corresponding heating moment is poorly defined;

The absorbance of the products 1 is not close to 100% in this spectral range. For paper that is medium clear in color or white, it reflects or diffuses the bulk of the energy. The heating is therefore only 5% to 10% of the preceding value, or about 0.25° C. for a cardboard of 200 µm, and 1° C. for a paper of 50 µm.

This then approaches the detection limit of low-resolution cameras, and the differential mode (control image before heating) becomes essential. This radiation mode, however, is advantageous for reducing the lighting number in a multi-sensor application.

A third possibility for carrying out the controlled heating within the scope of the invention consists in implementing a pulsed lighting or lighting by repeated pulses.

Heating means based on repetitive flashes of short duration (1 ms, and even 10 µs) exist. It is possible to produce these flashes with Xenon lamps, or movie projectors. However, these flashes are in general optimized to operate in the visible domain, and their yield in infra-red means is relatively low. Despite this drawback, they offer the advantage of a moment of perfectly defined heating.

A fourth concrete possibility for carrying out the controlled heating of the objects 1 as they pass consists in implementing lighting by laser, preferably infra-red.

Lighting by laser, combined with a controlled two-dimensional scanner, is certainly more complex, but it offers several advantages relative to thermal sources as indicated below.

First of all, it makes it possible to simplify the differential heating analysis by bringing it to a single image. If a particular tip of the object that is briefly heated with the laser is targeted, it is possible to evaluate the heating at the end of a period of 100 to 200 ms. As was seen above, this time is sufficient so that the heat diffuses into the thickness of the object, but not for a lateral diffusion. It is therefore possible to compare the heated zone directly to the adjacent zones, which are also thermally balanced. The order of magnitude of the size of the zones that are suitable is from 5 to 10 mm on a side or in diameter, which is perfectly compatible with commercial collimated laser beams.

A variant consists in creating a heated line with the laser by leaving an adjacent line unheated. To take into account the unavoidable defocusing of the thermal camera caused by the stream, whose acquisition time is several milliseconds, corresponding to 10 to 20 mm of passage, it is advantageous for this line to be parallel to the direction of advance of the conveyor belt.

The laser makes it possible to concentrate the energy on the zones of interest and therefore to reduce significantly the energy needs, as well as the associated fire risks. If the laser is placed downstream from a vision system that has located the objects, it can be directed only to the points where the objects are present. By combining with the preceding arrangement, it is possible to scan the lines that are parallel to the advance of the conveyor belt 3, but only where objects 1 are present.

This second preferred method of operation is illustrated by the diagram of FIG. 3. A laser 5" creates a collimated beam, a beam that is deflected by a set of two mirrors with perpendicular axes 8 toward an object 1, where alternating heated/non-heated lines are described, lines that are preferably parallel to the direction of advance D of the objects. The laser can operate continuously or in pulsed mode. Before the image acquisition, the objects 1, as before, are allowed to stabilize their temperature during the transit of distance d. The control zone 7" is no longer necessary.

With this production, any heating of the conveyor belt 3 is avoided, and the energy requirements are reduced drastically. If a filling rate of the belt of about 20% is assumed, and if 50% of the surface of each object is heated, 10% of the preceding energy is sufficient to obtain an equivalent thermal effect. An energy of 200 W instead of 2000 W is therefore sufficient. If a "survey" of 10% of the surface of each object, which is entirely realistic, is satisfactory, 40 W is sufficient. If a heating of 1° C. in the case of a thick product (200 μm) and of 4° C. for a thin product (50 μm) are considered to be sufficient, the requirements are also reduced by a factor of 4. The smallest laser that is suitable for the application then has a power of 10 W.

Finally, the laser, because of its nature, offers other advantages:

By its monochromatic nature, it makes it possible to act specifically on certain materials whose absorption can be maximum at the wavelength of the laser;

It even makes it possible to select the length of time of heating of the object based on other criteria, such as the constituent material, if this indication is provided in advance by another sensor 10, such as an infra-red spectrometer.

Below, various applications of the process and the machine according to the invention will be presented in connection with various types of object-sorting.

A first application of the invention relates to papers, in particular the differentiation between printed forms and cardboard-type packaging products.

This application involves a structured (fibrous) product that is greatly diffusing and opaque. In the MIR wavelengths, it is very absorbent, and its emissivity is high (>0.9) and constant.

The differentiation should relate to two printed products of close appearance:

Small packaging cardboards whose thicknesses vary from 250 to 400 μm,

Magazines and advertisements: their inside sheets have thicknesses of approximately 40 μm, but the covers, which are seen more frequently, reach 150 μm.

For the diffusivity of paper: $a=0.14$ mm$^2$/s is assumed, and for

Small thin cardboards: $Th\_c=e^2/2 \cdot a=0.25^2/(2 \times 0.14)$ s=0.224 s=224 ms is assumed, and for Magazine covers: $Th\_m=0.16^2/(2 \times 0.14)=92$ ms is assumed.

An image is taken after stabilization or here after 224 ms, the longest homogenization time of the two products.

With a passage at 3 m/s, the movement is from about 670 mm between the two points. This is sufficient just to have the two image bands in the same image, if a 320×240-pixel camera is assumed, with pixels whose image on the belt has 4 mm on the side.

Heating with MIR radiation of approximately 5.6° C. is calculated for the magazine cover and of 3.6° C. for the small cardboard. The difference of these values is significant and measurable.

Finally, it is necessary to take into account the influence of the moisture: it greatly increases the thermal capacity and therefore is equivalent to a greater thickness. Any very wet paper will therefore tend to be confused with a cardboard. This case is compatible with the recycling objectives, because contaminated products are not desired, and they are almost always wetted. Therefore, the sorters tend to discard wet papers.

Finally, for very thin products, such as isolated paper sheets (or plastic films that are placed on the conveyor belt), it is the conveyor belt itself and its higher temperature that show through the object: this tends to make the product be classified even more as a paper. The effect is therefore favorable, except for plastic films.

A second application of the invention relates to the products—in particular the packages—that are made of a multilayer polymer material (PET).

The distinction is to relate above all here to uncolored transparent bottles, which are produced either in a single PET layer, or in at least three juxtaposed layers, whereby the center layer consists of a material that forms a barrier to a gas ($O_2$ or $CO_2$). This material is, for example, nylon. Another case depicted, close but simpler, is the presence of labels or plastic sleeves on the surface, even after washing. In this case, it is necessary to characterize the presence of the label on the surface.

After heating a multilayer, the heat penetrates primarily the first thickness (surface layer). Actually, the layers are not made integral, and the conduction toward the second layer is very limited. The phenomenon is accentuated by the fact that during the heating, the optical discontinuity creates an upward reflection of a portion of the incident energy.

A single-layer bottle generally has a thickness of approximately 400 μm. If it is three-layer, the central layer is thin, or approximately 20 μm, and it separates two layers of about 190 μm each.

Single-layer: $Th\_m=e^2/2 \cdot a=0.4^2/(2 \times 0.14)$ s=0.571 s=571 ms.

Three-layer (first layer): $Th\_t=0.19^2/(2 \times 0.14)=129$ ms.

It is therefore necessary to wait for at least 250 ms to differentiate between the two cases, and ideally 570 ms, corresponding to a movement of 1500 mm. This last value prevents the two images from being processed with the same camera 6.

This said, it is possible to work at the washing output, typically carried out at 95° C., in the natural cooling of objects toward 30° C. The three-layer bottle cools on the surface faster than the single-layer. Then, only a single image is necessary.

A third application of the invention relates to the sorting of bags and films that are made of plastic material.

Most often, the plastic films are made of PE- or PP-type polyolefins, and they are difficult to distinguish by spectroscopy of the solid objects that are made of the same materials. In particular, the HDPE with an internal layer of carbon black, a particular type of multilayer, have spectra that are very close to the LDPE plastic bags. It then is possible, as for the preceding case, to sort them via differences in thickness, which are very significant. This type of sorting comes in addition to an infra-red spectrometer that has already determined the presence of PE (LD or HD). Since their thermal inertia is low, the image acquisition is to be done quickly after the heating zone for an ideal contrast, before the total stabilization of the HDPE bottles.

A fourth application of the invention relates to the purification of compost.

First of all, a stream of primarily organic products is obtained by screening starting from a stream of crude wastes. In general, an 80 mm mesh makes it possible to obtain from the fines (passing fraction) a stream that is concentrated to more than 80% organic material (food scraps, kitchen scraps, green waste), i.e., highly aqueous fines.

Two types of pollutants are encountered primarily:

Light pollutants: plastic types (flexible or rigid), and more or less contaminated papers;

Heavy pollutants: glass, rocks, metals, ashes.

Two successive images to visualize the heating are initiated again.

The products in question are nearly all opaque and therefore readily absorb the caloric radiation in a narrow surface layer.

The biological products resemble a skin that covers a captive water mass. They diffuse quite slowly (diffusivity of the water=0.14 mm²/s). Their thickness is at least 1 mm. The thermal capacity of water is the highest of all flow bodies. These products therefore have a lower equilibrium temperature.

The minerals and the glasses have a lower thermal capacity than water. However, they are always thick (>2 mm) and diffuse at least four times faster than water: they therefore quickly become colder than water, and this is visible from the heating phase.

The metals have a strong reflectivity (90 to 95%), and they heat very little. In addition, their emissivity is low, and for a given heating, they emit very little radiation: they therefore appear almost black. This is true from the control photo (before heating), if they are in thermal equilibrium.

The light pollutants are very sensitive to an MIR-type radiation, as already indicated above: they have little thermal capacity, and they are thin. Next, they diffuse slightly and keep an almost constant temperature for several seconds.

If the heating between the two images is shown by decreasing order, there will therefore be:
The hottest: plastics and papers;
The biological products, moderately heated;
The minerals and the glasses, slightly heated;
The metals, almost black, and this from the first image.

The strategy is a little different from the preceding cases: an adequate time is allowed to elapse to stabilize the papers, or approximately 200 to 250 ms. The other products are not yet stabilized. In contrast, even the plastics are already much hotter than the aqueous products because the calorific capacity of the water has lowered the temperature of the latter. For the same reasons, the glasses, minerals and metals are clearly colder and/or darker than the aqueous products.

It is then decided to eject all of the very hot and very cold products by keeping the products of intermediate value. It is seen that this type of sorting can use only a thermal camera as a single sensor, which makes it very competitive.

Thus, the invention relates to the application of thermography cameras, combined with elements for heating by radiation, to perform the real-time sorting of various types of products, and in particular:
Differentiation of paper and cardboards on the basis of the thickness of the first layer;
Differentiation of single-layer and multi-layer plastic packages;
Differentiation of thick plastics (more than 1 mm) per material;
Differentiation of various pollutants (plastics, papers, metals, glasses, minerals) in a biological stream that is intended for composting.

As follows from the preceding, this invention proposes a simple method, suitable in the case of thin and non-metallic products, whose thickness is spread in the range of 20 µm-2 mm.

It makes use, in its preferred applications, of the following physical phenomena:
The calorific capacity per unit of surface area is directly proportional to the thickness of the surface layer of the heated material and therefore for a given surface radiation level, the temperature rise at equilibrium is inversely proportional to this thickness. It is possible to deduce therefrom the thickness for a known material;
The time periods that are necessary for reaching the thermal equilibrium are short enough (less than 500 ms) so that the other thermal phenomena (lateral conduction, cooling by radiation or convention) are negligible;
The thicknesses are sufficient to ensure an almost total absorption of the heating radiation, at least for certain wavelengths. Below 20 µm, these conditions are no longer complied with.

It is thus possible to differentiate products by their thicknesses for the purpose of sorting them into different categories. The time periods between heating and detection are, furthermore, short enough to allow a quick decision, and a real-time sorting with a compact machine, even for rapidly passing products.

Of course, the invention is not limited to the embodiments that are described and shown in the accompanying drawings. Modifications are possible, in particular from the standpoint of the composition of the various elements or by substitution of equivalent techniques, without thereby leaving the field of the protection of the invention.

The invention claimed is:

1. An automatic process for inspecting and sorting non-metallic objects that belong to at least two different categories and pass in an essentially single-layer stream on a conveying plane of a conveyor belt, comprising:
temporarily subjecting a surface layer (4) of said passing objects (1) to the caloric radiation of at least one remote heating means (5), so as to deliver to each of these passing objects (1) a non-altering heat pulse that is identical for all of the passing objects in terms of heat energy applied per unit of surface area in the conveying plane (2);
after a determined length of time has elapsed following the application of the heat pulse, acquiring at least one thermal image of each of said passing objects by means of at least one linear or matrix thermal sensor (6);
processing data contained in the acquired thermal image to determine a thickness of the surface layer (4) affected by the caloric radiation of the passing objects, and classifying each passing object (1) based on the data, and delivering a control or actuation signal for each passing object; and
separating the passing objects (1) based on at least one of i) a class or category and ii) the delivered control or actuation signal for each passing object,
wherein the constituent material of said surface layer (4) of the passing objects (1) is identical for all of the passing objects, and
wherein for each passing object (1), the determined length of time that elapses between an application of the caloric radiation and the acquisition of the thermal image is sufficient i) for said surface layer (4) to absorb an essentially homogeneous distribution of caloric energy such that a temperature difference after heating said passing objects on the surface is essentially inversely proportional to the thickness of this surface layer (4), and also ii) so that the phenomena of lateral thermal diffusion, cooling by radiation and convection are negligible.

2. The process according to claim 1, wherein the discrimination or the characterization of said passing objects (1) is carried out on the basis of differential data or by differential exploitation of data, obtained either from thermal images that are taken before and after application of the caloric radiation that is emitted by the heating means (5) or from a single thermal image taken after application.

3. The process according to claim 1, wherein the heat pulse affects the surface layer (4) of each passing object (1) over an entirety of the surface layer.

4. The process according to claim 1,
wherein the surface layer (4) has a thickness of more than 20 μm, and
wherein a length of time that elapses between the application of the caloric radiation and the thermal imaging is several tenths of a second.

5. The process according to claim 4, wherein the surface layer (4) has a thickness between 20 μm and 2 mm.

6. The process according to claim 4, wherein the length of time that elapses between the application of the caloric radiation and the thermal imaging is between 50 ms and 600 ms.

7. The process according to claim 6, wherein the surface layer (4) has a thickness between 30 μm and 1 mm.

8. The process according to claim 6, wherein the length of time that elapses between the application of the caloric radiation and the thermal imaging is between 250 ms and 400 ms.

9. The process according to claim 1, further comprising:
thermal imaging of each passing object (1) before the subjecting of the caloric radiation, whereby the discrimination or the characterization of said passing objects (1) is performed based on differential data that are obtained from said thermal images taken before and after application of the caloric radiation emitted by the heating means (5), whereby the images before and after the subjecting of the caloric radiation are taken by the thermal sensor (6) or by two different sensors.

10. The process according to claim 1, wherein a deposit of caloric energy that results from the application of the radiation that is emitted by the heating means (5) is essentially uniform and spread out evenly over an entire exposed surface (7) at a level of the conveying plane (2).

11. The process according to claim 1, wherein the deposit of caloric energy that is carried out by the radiation that is emitted by the heating means (5) is by nature intermittent and is limited to localized zones of an exposed surface (7) at a level of the conveying plane (2).

12. The process according to claim 11, wherein the discrimination or the characterization of each passing object (1) is performed based on a single thermal image taken after exposure by differential exploitation of data of the irradiated and non-irradiated zones of the surface, and therefore of the surface layer (4) of each passing object (1).

13. The process according to claim 11, wherein the deposit of caloric energy is limited to segments of lines extending in a direction of movement of the passing objects.

14. The process according to claim 1, further comprising:
acquiring additional data relating to the passing objects (1) by means of at least one additional sensor (10), wherein the additional data are combined with the data contained in the thermal image or images to perform the discrimination or the characterization of said passing objects (1).

15. The process according to claim 14, wherein the at least one additional sensor (10) is selected from the group consisting of magnetic detectors, spectrometers, and vision cameras.

16. The process according to claim 1, wherein the thermal sensor (6) is a thermal camera.

17. The machine according to claim 1, wherein the tubular radiation source (5") emits a radiation in the middle infra-red range.

18. The machine according to claim 17, wherein the tubular radiation source (5") emits a radiation with in the infra-red range with wavelengths longer than 2000 nm.

19. The process according to claim 1, wherein the caloric radiation consists of mostly infra-red radiation.

20. An automatic machine for inspecting and sorting non-metallic objects, said objects belonging to at least two different categories and passing in a direction and in an essentially single-layer stream on a conveying plane of a conveyor belt, comprising:
at least one remote heating means (5) configured to temporarily subject a surface or outside layer (4) of said passing objects (1) to caloric radiation so as to deliver to each of said passing objects a non-altering heat pulse that is identical for all of said passing objects in terms of thermal energy that is applied per unit of surface area in the conveying plane (2);
at least one linear or matrix thermal sensor (6) placed at a predetermined distance (d) downstream from said at least one heating means (5) in the direction of passing, the at least one thermal sensor (6) configured to acquire at least one thermal image of each of said passing objects; and
at least one processing unit (12) for performing a discrimination or characterization of said passing objects (1), the at least one processing unit (12) configured to determine a thickness of said surface layer (4) based on data contained the at least one acquired thermal image, to classify each of said passing objects (1) based on the determined thickness, and to deliver a control or actuation signal for each passing object, said at least one processing unit (12) being connected to at least one means (13) for separating said passing objects (1) based on i) a category or class, and ii) the delivered control or actuation signal,
wherein the predetermined distance (d) separating a heating zone (7) in which the thermal energy is applied and a zone in which the at least one thermal image is acquired of each of said passing objects is determined based on a length sufficiently long so that a caloric energy absorbed in the surface layer (4) of each passing object (1) has an essentially homogenous distribution in the surface layer, and also sufficiently short so that effects of lateral thermal diffusion, cooling by radiation, and cooling by convection are negligible, and
wherein the constituent material of at least the surface layer (4) of the passing objects (1) is identical for all of the passing objects (1).

21. The machine according to claim 20, wherein the processing unit (12) performs the discrimination or the characterization of said passing objects (1) based on differential data or by differential exploitation of data, obtained either from thermal images that are taken before and after application of the caloric radiation that is emitted by the heating means (5) or from the thermal image taken after application.

22. The machine according to claim 20,
wherein the conveyor belt (3) that forms the conveying plane (2) has a constant displacement speed, and
wherein said at least one heating means (5) and said at least one thermal sensor (6) are placed above said conveying plane (2).

23. The machine according to claim 20,
wherein the thermal sensor or sensors (6) carries or carry out, for each passing object (1), an imaging before and after exposure of said object to a caloric radiation (5'), and
wherein the processing unit (12) performs discrimination or categorization of said passing objects (1) on the basis of differential data obtained from their thermal images that are acquired before and after exposure to said caloric radiation (5').

24. The machine according to claim 20, wherein the heating means (5) comprises a laser source (5"), of the continuous or intermittent emission type, combined with an application device (8) with two-dimensional scanning, configured to deposit the caloric energy in a discontinuous nature limited to localized zones of an exposed surface of the heating zone (7) at the level of the conveying plane (2).

25. The machine according to claim 24, further comprising:
a device for locating and delimiting the apparent surface of the passing objects (1) on the conveying plane (2) that is located upstream from the heating means (5) in the direction of passage configured to acquire a data for locating and delimiting an apparent surface to control said heating means (5).

26. The machine according to claim 24, wherein the deposit of caloric energy is limited to segments of lines extending in a direction of movement of the passing objects.

27. The machine according to claim 24, wherein the processing unit (12) performs discrimination or characterization of each passing object (1) on the basis of the single thermal image taken after exposure, by differential exploitation of the data of the irradiated and non-irradiated zones of the exposed surface and therefore of an exposed portion of the surface layer (4) of each of the passing objects.

28. The machine according to claim 20, further comprising:
at least one additional sensor (10) selected from the group consisting of magnetic detectors, spectrometers, and vision cameras,
the at least one additional sensor (10) configured to acquire additional data to be combined in the processing unit (12) with the data of the thermal image or images to perform the discrimination or the characterization of said passing objects (1).

29. The machine according to claim 20, wherein the thermal sensor (6) is a thermal camera.

* * * * *